(12) United States Patent
Kuehhorn et al.

(10) Patent No.: US 8,024,137 B2
(45) Date of Patent: Sep. 20, 2011

(54) METHOD FOR DETERMINING BLADE MISTUNING ON INTEGRALLY MANUFACTURED ROTOR WHEELS

(75) Inventors: Arnold Kuehhorn, Berlin (DE); Bernd Beirow, Cottbus (DE)

(73) Assignee: Rolls-Royce Deutschland Ltd & Co KG (DE)

( * ) Notice: Subject to any disclaimer, the term of this patent is extended or adjusted under 35 U.S.C. 154(b) by 567 days.

(21) Appl. No.: 12/078,608

(22) Filed: Apr. 2, 2008

(65) Prior Publication Data

US 2010/0286934 A1   Nov. 11, 2010

(30) Foreign Application Priority Data

Apr. 3, 2007  (DE) .......................... 10 2007 016 369

(51) Int. Cl.
*G01N 11/16* (2006.01)
(52) U.S. Cl. ............................................. 702/56; 702/85
(58) Field of Classification Search .................... 702/10, 702/54, 56, 85; 73/1.14, 457, 459, 460; 416/223 A; 249/152
See application file for complete search history.

(56) References Cited

U.S. PATENT DOCUMENTS

| | | | |
|---|---|---|---|
| 3,582,036 A * | 6/1971 | Condis | .......................... 249/152 |
| 6,629,463 B2 | 10/2003 | Naudet | |
| 7,082,371 B2 | 7/2006 | Griffin | |
| 7,497,664 B2 * | 3/2009 | Walter et al. | .............. 416/223 A |
| 2004/0243310 A1 * | 12/2004 | Griffin et al. | ................... 702/10 |

OTHER PUBLICATIONS

Pierre, Christophe, et al.: Experimental Investigation of Mistuned Bladed Disk Vibration. In: Proceedings of the 5$^{th}$ National Turbine Engine Gigh Cycle Fatigue Conference, Chandler, Arizona, Mar. 2000, pp. 1-7.
Server, I.A.: Experimental Validation of Tubomachinery Blade Vibration Predictions. Ph.D.-thesis, University of London (Imperial college) 2004.
Beirow, B.: Experimentelle and numerische Untersuchungen hinsichtlich einer Festigkeitsauslegungsoptimierung von Hochdruckverdichterschaufelscheiben unter besonderer Berucksichtigung von Mistuningeffekten, DLRG-Kongress 2003, ISSN 0700-4083.

* cited by examiner

*Primary Examiner* — John H Le
(74) *Attorney, Agent, or Firm* — Timothy J. Klima; Shuttleworth & Ingersoll, PLC

(57) ABSTRACT

For determining production-inherent mistuning of integrally manufactured rotor wheels (blisks) on the basis of the identification of blade natural frequencies, the individual blades are excited independently of each other and the vibratory response is measured for the calculation of the respective blade natural frequency and of mistuning. During measurement the blades not under investigation are additionally mistuned by temporarily applying an identical extra mass to each of them, such that coupling effects disturbing the measurement of the vibratory response of the excited blade are shifted away from the natural frequency-near range of the blades and hence eliminated.

10 Claims, 5 Drawing Sheets

METHOD FOR DETERMINING BLADE MISTUNING ON INTEGRALLY MANUFACTURED ROTOR WHEELS

Figure 1:
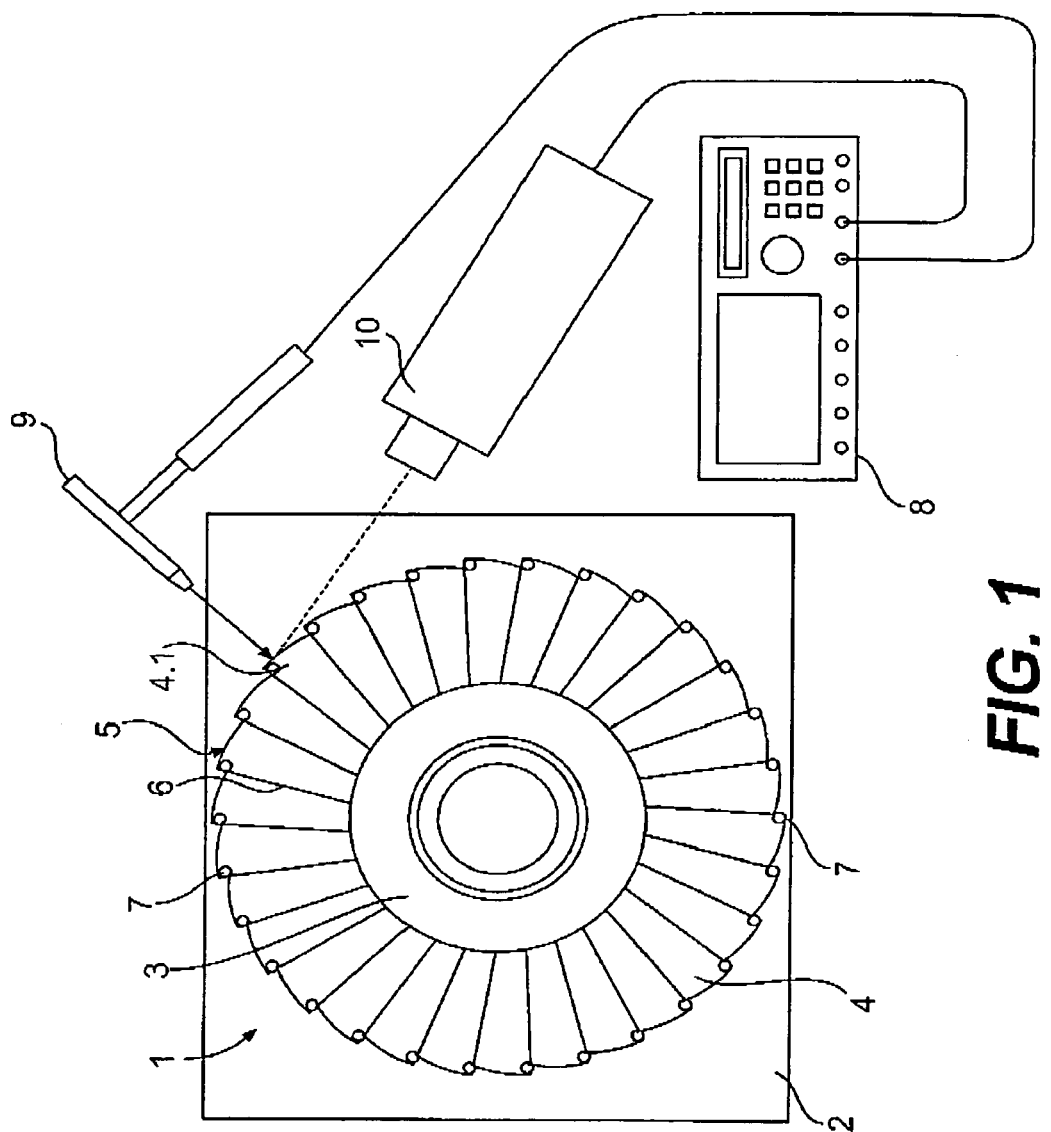

This application claims priority to German Patent Application DE 102007016369.1 filed Apr. 3, 2007, the entirety of which is incorporated by reference herein.

This invention relates to a method for determining blade mistuning on integrally manufactured rotor wheels for compressors and turbines, in particular for gas-turbine engines, in which the individual blades are pulse-excited one after the other in a condition largely decoupled from the other blades, with the vibratory response of the respective blade being measured.

In compressor and turbine engineering, in particular in the aircraft engine sector, integrally formed rotor wheels, termed blisks, are increasingly used. Compared with the conventional design, integrally formed rotor wheels are capable of higher rotational speeds, thus providing for improved pressure ratio and more powerful engines. Integrally manufactured rotor wheels are increasingly employed also on compressors and turbines outside the aircraft sector. However, the one-piece design gives rise to production-inherent disturbances of the rotational symmetry, i.e. unbalance of the entire structure. This peculiarity of blisk-type rotor wheels, which is also referred to as mistuning, is reflected in specific blade natural frequencies and entails vibration amplitude and strain excesses in the blades due to aerodynamic excitation, resulting in fatigue affecting the life of the rotor wheel. Therefore, a determination of the blade natural frequencies—as closely as possible to reality—enables production-inherent disturbances of the rotational symmetry of the rotor wheel, i.e. mistuning of the entire structure, to be identified and corresponding statements on the quality of the respective blisk to be made regarding its vibratory behavior under operating conditions as well as its operational safety and service-life.

U.S. Pat. No. 7,082,371 B2 describes a method for determining mistuning of rotating blade structures, more particularly for predicting the vibratory behavior of integrally manufactured rotor wheels (blisks) of gas turbines. A software is capable of describing normal modes and natural frequencies of the blisk, actually by using tuned system frequencies and the frequency mistuning of each blade/blade sector. In this method, which is known as FFM (Fundamental Mistuning Model), normal, i.e. untuned, modes and natural frequencies of the respective blisk are used to determine sector frequencies as well as tuned system frequencies. FMM is capable of predicting how much the blisk will vibrate during rotation under operating conditions. The method includes obtaining nominal frequencies of a tuned blisk system, measuring of at least one untuned mode and calculating mistuning of at least one blade of the blisk on the basis of the nominal frequencies and of said, at least one, untuned mode and of the natural frequency. The quantities required for calculation can advantageously be obtained on a system in free, unchanged condition. However, FFM is only suitable for strongly coupled systems with a low number of blades. If the number of blades is high, natural modes corresponding to the number of blades will occur within a frequency band of a few Hz which conflict with a sufficiently precise separation of modes or require separation by extremely costly methods, respectively.

In another known method for determining mistuning of blisks, or predicting airfoil vibrations of a blisk during operation (Sever, I.A.: Experimental Validation of Turbomachinery Blade Vibration Predictions, Ph.D.-thesis, University of London (Imperial College), 2004) the disk is clamped between solid steel blocks. Additionally the blades which are currently not measured, are also restrained with considerable investment to reduce the coupling effects between the blades during excitation and vibration measurement and enable the natural frequency of the respective blade to be actually measured. According to yet another investigation into the strength design of bladed disks (Beirow, B. et. al. Experimental and numerical investigations regarding strength design optimization of bladed high-pressure compressor disks considering mistuning effects (Experimentelle und numerische Untersuchungen hinsichtlich einer Festigkeitsauslegungsoptimierung von Hochdruckverdichterschaufelscheiben unter besonderer Berücksichtigung von Mistuningeffekten), DGLR-Kongress 2003, München 2003, ISSN 0700-4083), only the disk is restrained, and the individual blades of the blisk are excited one after the other by pulse excitation, with the vibratory response being simultaneously measured by a contactless method. Thus, a relatively good identification of relative (related) mistuning distributions on blisks is principally possible on fully or partly decoupled rotor wheels in blisk design. However, with decoupling being incomplete, definite vibratory responses which correspond to the actual conditions in operation are not obtainable. Apart from the fact that such restraint incurs considerable effort and investment, the above methods can only be used on rotor wheels to which such restraint can actually be applied, i.e. where it does not conflict with blisk geometry, for example in the case of a high number of blades or with the installed state of the rotor wheels.

In a broad aspect, the present invention provides a method of the type specified at the beginning for determining blade mistuning of blisk-type rotor wheels which, irrespective of rotor wheel design and also in the installed state of the rotor wheel, ensures adequate decoupling between the respective blade under investigation and the disk as well as the other blades, with low effort, thereby providing for a definite, realistic vibratory response of the respective blade excited and, finally, permitting a definite statement to be made on the blade natural frequency distribution and, thus, rotor wheel mistuning.

In other words, the basic idea of the present invention is that, in a method, the blades of the integrally manufactured rotor wheel—except for that blade that is excited for measurement of the vibratory response—are further mistuned by temporarily fitting each with an identical extra mass. Thus, the vibration frequency of the blades which are not under investigation is shifted from the natural frequency-near range of the blades, thereby essentially avoiding disturbing or falsifying coupling effects in the vibratory response of the blade under investigation. In this way, the natural frequency of the individual blades, and thus blade natural frequency distribution on the rotor wheel and mistuning of the entire structure, are realistically determinable. Amplitude and strain increases in operation involved with unavoidable, production-inherent mistuning are detectable beforehand, enabling reliable statements regarding the problem of fatigue as well as service-life and operational safety of the blisk to be made.

In accordance with a further important feature of the present invention, a specific extra mass is required to obtain additional blade mistuning, with the size of this mass depending on the design blade mass, the design blade frequency of the blade modes and the expected magnitude of blade mistuning.

In a further embodiment of the present invention, transfer functions are determined on the basis of the measured vibratory response signals for each blade and mode family from which the maximum frequencies pertaining to the respective amplitude maxima can be read. From these, an average value will be calculated which finally serves as reference for representing the blade natural frequency distribution or mistuning of the rotor wheel, respectively.

In an advantageous development of the present invention, the average values, which are calculated slightly too small, are correctable in dependence of blade stiffness and design blade mass using a mass-spring-damper model as an equivalent rotor wheel model.

In an embodiment of the present invention, the extra mass is provided in the form of small metallic cylinders fixed with beeswax to corresponding locations on the blades which are not under investigation. The impact pulse for blade excitation is in each case produced at the same location and under the same angle using a miniature hammer. The vibratory response of the excited blade is recorded contactless by laser vibrometry.

The method is applied to blisk-type compressor and turbine rotor wheels, in particular compressor rotor wheels of aircraft gas turbines, actually in the removed state in virtually free condition, or also in the installed state, of the rotor wheel.

Figure 2:
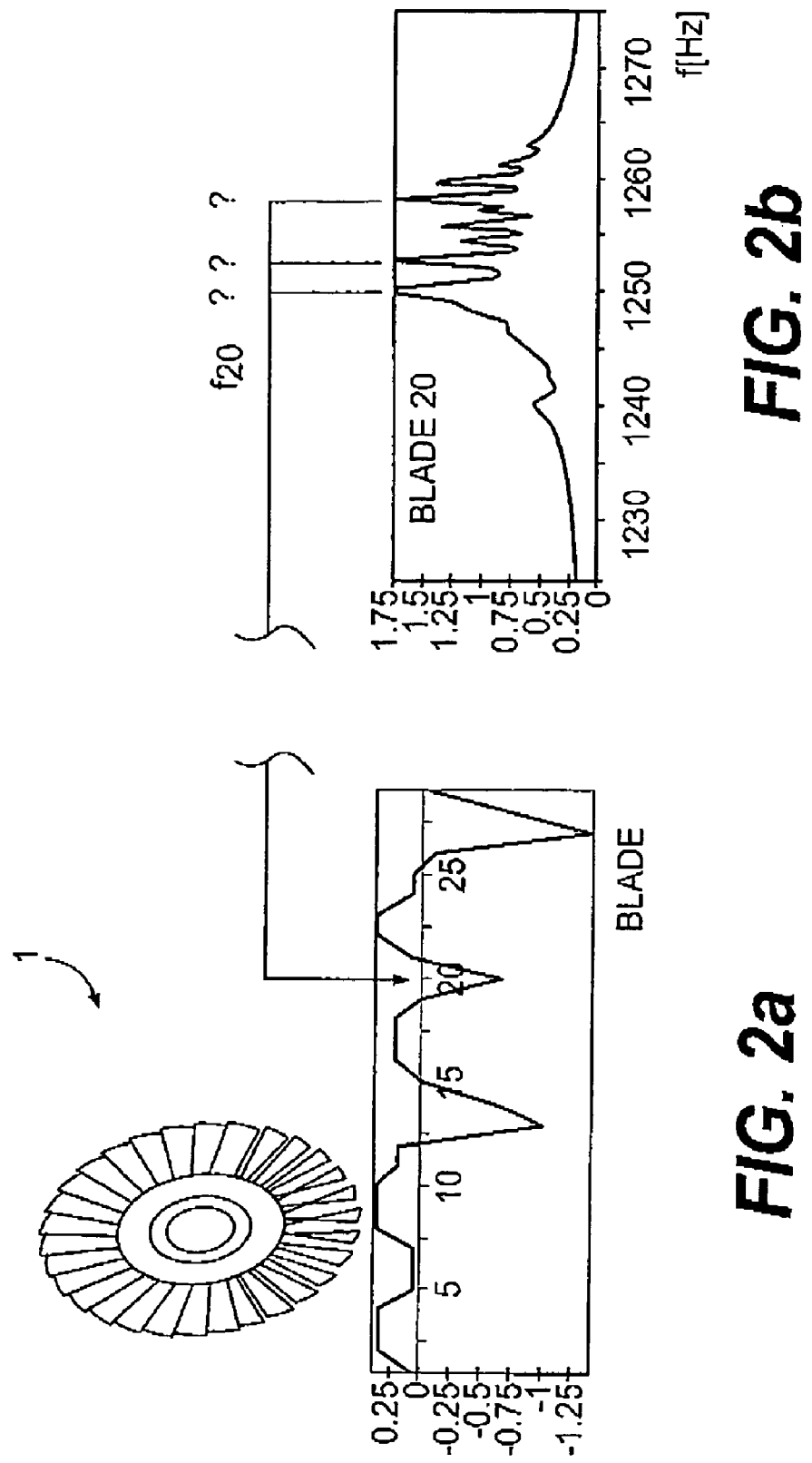
Figure 3:
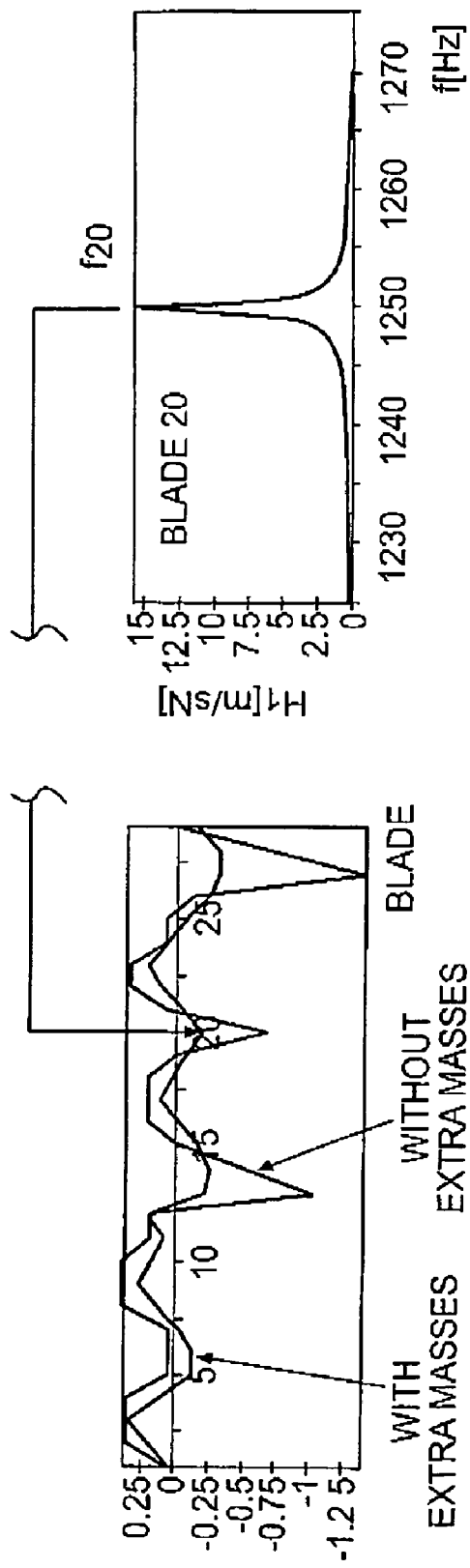
Figure 4:
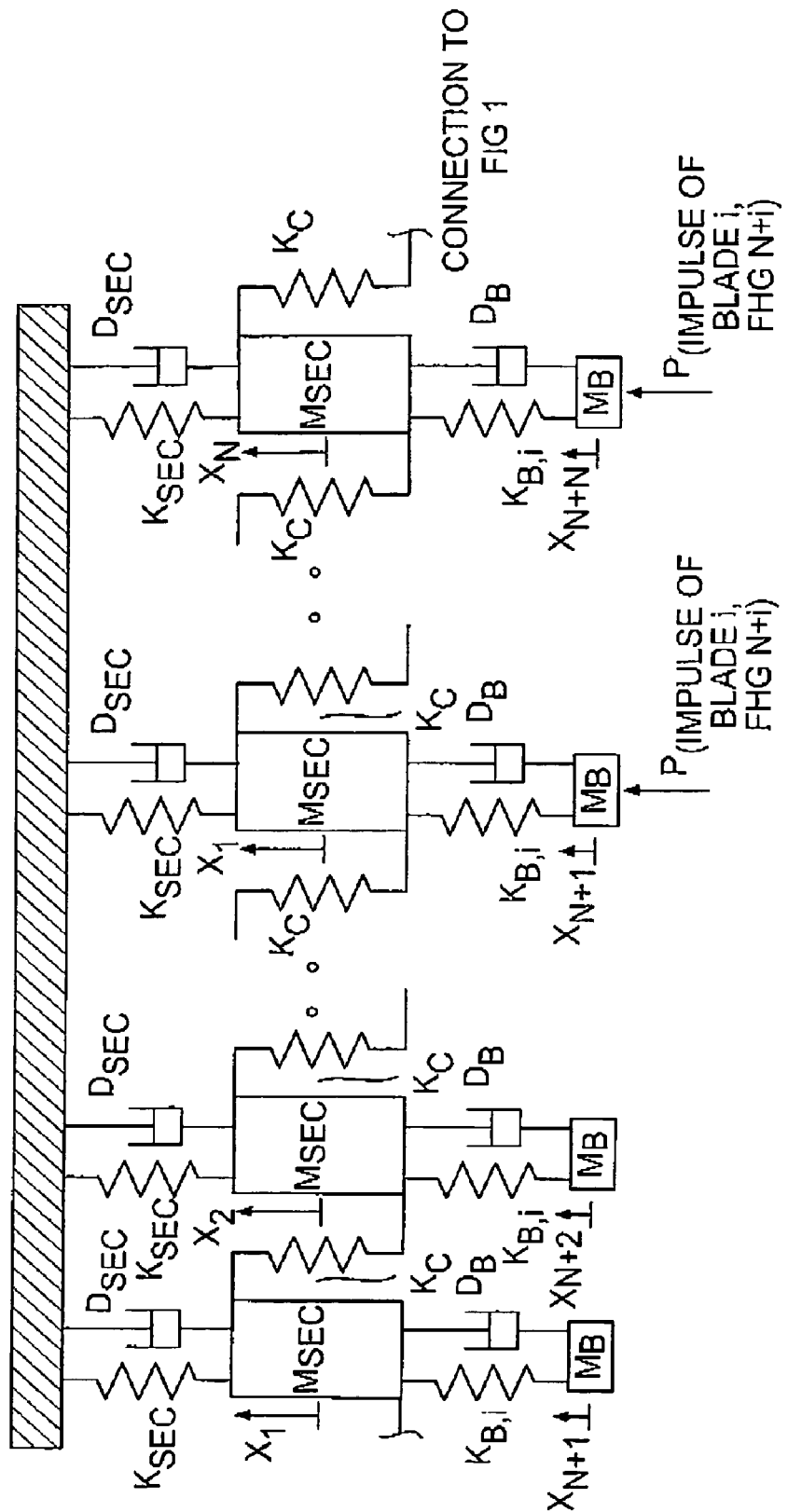
Figure 5:
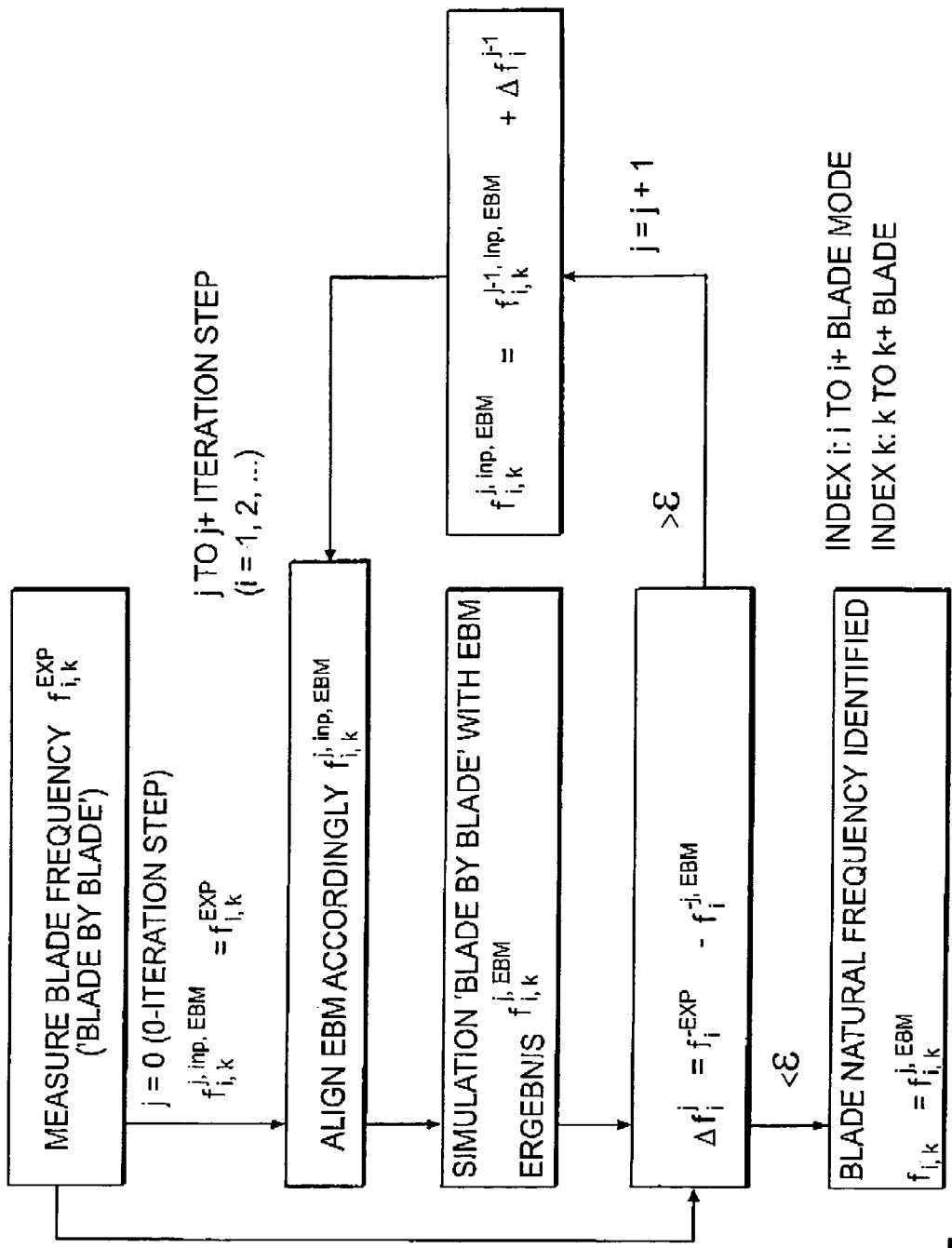

The present invention is more fully described in the light of the accompanying drawings showing a preferred embodiment. In the drawings:

FIG. 1 is a schematic representation of the arrangement for the determination of blade mistuning on a blisk-type rotor wheel of the high-pressure compressor of an aircraft gas turbine, FIG. 2 (Prior Art) is a graphic representation a) of a transfer function with an amplitude maximum for part of the blades of the rotor wheel and b) of another form of representation of the transfer function for a single blade with the maximum frequency being referred to the amplitude maximum of a blade, actually with a blisk not sufficiently decoupled in accordance with the state of the art, FIG. 3 is a graphic representation of the transfer functions as per FIG. 2, however with blades decoupled in accordance with the present invention using extra masses for clearly identifying the natural frequency of the respective blade, FIG. 4 is an equivalent blisk model (EBM) for optimum calculation of the correction of the frequency average value, and FIG. 5 is a block diagram for iterative correction of blade frequency distributions determined by measurement.

As shown in FIG. 1, the blisk-type rotor wheel 1 to be examined is placed on a foamed plastic mat 2 to provide a virtually free condition. The rotor wheel 1 comprises a disk 3 which has blades 4 integrally formed onto its outer circumference. With the exception of the blade under investigation 4.1, all other blades 4 have specific, identical extra masses 7 in the form of small metallic cylinders fixed to them at always the same location, here in the area between blade tip 5 and blade leading edge 6. The respective extra mass 7 is fixed to a side of the blade by means of an easily removable bonding agent, here beeswax, applied to a face of the metallic cylinder. The respective blade under investigation 4.1 is excited by means of an impact mechanism, here in the form of an impulse hammer 9, connected to a control unit 8 by applying a miniature hammer impact pulse. The vibratory response of the respective blade 4.1 is recorded contactless by laser Doppler vibrometry using a measuring device, here a single-point laser vibrometer 10 connected to the control unit 8. Since the other blades 4 are additionally mistuned by means of the extra masses 7, disturbing coupling effects arising at these blades, because of the strong blade-disk coupling on blisks, are shifted away from the interesting frequency range lying in the vicinity of the blade natural frequency to be measured, enabling mistuning of the respective blade under investigation 4.1 to be established on the basis of the blade natural frequency determined. Subsequently, the other blades 4 will in the same manner be subjected to the investigation—in each case without extra mass 7. The impact pulse is applied to the respective blade under investigation 4.1 always at the same location, under the same angle and with the same magnitude.

The size of the extra mass $\Delta m$ (g) is determined in dependence of the design blade mass $m_b$ (g), the design blade natural frequency of the $i^{th}$ blade mode $f_{0,i}$ (Hz) and the expected magnitude of blade mistuning, i.e. the proportional mistuning span of the $i^{th}$ blade mode $\Delta f_{span} = \Delta f_{max} + \Delta f_{min}$ (%), with $\Delta f_{max} = (f_{i,max} - f_{0,i})/f_{i,max}$ (%) being the positive maximum of mistuning and $\Delta f_{min} = (f_{i,min} - f_{0,i})/f_{i,min}$ (%) being the negative minimum of mistuning of the respective $i^{th}$ blade mode, established as follows:

$$\Delta m > m_b \left[ \left[ \frac{1}{1 - \frac{|\Delta f|_{span} \div 100}{f_{0,i}}} \right]^2 - 1 \right]$$

This is a conservative estimate since the effectively co-vibrating blade mass assumes a smaller value compared to the actual design blade mass $m_b$.

A transfer function is now calculated from the force input signals and the vibratory response signals for each of the, for example, 80 blades of the blisk 11 of a high-pressure compressor and each family of modes ($1^{st}$ bending, $2^{nd}$ bending, $1^{st}$ torsion, $2^{nd}$ torsion etc.). The maximum frequencies $f_i$ pertaining to the amplitude maxima (FIG. 3b), which occur isolated in the transfer functions H[m/s/N] due to the blade under measurement being decoupled from the other blades fitted with extra masses, are used as input values for the relative blade natural frequency distribution $(f_i - f_{i,mean})/f_{i,mean}$ (FIG. 3b). The blade natural frequency distribution of the blisk so determined for all families of modes enables reliable statements to be made on blade mistuning or blade behavior in operation and, finally, on the quality and service-life of the blisk.

To illustrate the disadvantages of the state of the art, FIG. 2a shows the transfer function of the vibratory responses of the blisk blades on the basis of transfer functions determined by measurement. The representation of a transfer function H[m/s/N] for the amplitude maximum of a single blade (no. 20) in FIG. 2b clearly shows that the blade natural frequency is not definitely identifiable due to coupling effects, as a result of which a reliable assessment of the blisk is not possible. However, with extra masses 7 being used, the blade natural frequency on blade no. 20 is definitely identifiable due to the single frequency maximum (FIG. 3b) pertaining to the respective amplitude maximum (FIG. 3a). The blade frequency distributions determined by the above method can be used to tune a finite element model and, thus, to calculate forced vibratory responses which, finally, supply information substantial for optimum positioning of strain gauges.

Since the average values $f_{i,mean}$ calculated in the above for the representation of the related blade frequency distribution are calculated slightly too small due to unavoidable coupling effects and the extra masses used, correction of the average value to even more accurately represent the blade natural frequency distribution is provided by using a mass-spring-damper model. (Beirow, B. et. al. Localisation phenomenon on high-pressure compressor rotor disks (Lokalisierungsphänomen bei Hochdruckverdichterschaufelscheiben) VDI-Reports No. 168, 2006, ISBN 3-18-091968-X). Such an equivalent blisk model (EBM) is depicted in FIG. 4. The information necessary for correction is obtained by means of a numerical experiment. For this, the frequency distribution determined by measurement is given to the model via automated adaptation of the blade stiffness $k_{b,i}$ in, for example, a FORTRAN code, and the pulse excitation of the measurement is simulated. The distribution determined by means of a time-step integration method will, on average, be below the specified measurement, so that an iterative increase of the blade stiffness according to FIG. 5 is required until the frequencies determined by measurement are reached. The iteration process shown in FIG. 5 can be accomplished selectively on one or a few blades to reduce computation time.

The distribution of the blade stiffnesses $k_{b,i}$ adapted in this way, together with the known design blade mass $m_b$, defines the blade natural frequency distribution of the blisk with regard to the family of modes under examination via:

$$f_{b,i} = \frac{1}{2\pi}\sqrt{\frac{k_{b,i}}{m_b}},$$

which simultaneously corresponds to the model specification of the last iteration step. With the blade natural frequency distribution so determined, blade mistuning is described with sufficient accuracy.

| List of reference numerals | |
| --- | --- |
| 1 | Rotor wheel |
| 2 | Foamed plastic mat |
| 3 | Disk |
| 4 | Blades with extra mass |
| 4.1 | Blades without extra mass |
| 5 | Blade tip |
| 6 | Blade leading edge |
| 7 | Extra mass |
| 8 | Control unit |
| 9 | Impulse hammer |
| 10 | Single-point laser vibrometer |
| $\Delta m$ | Size of extra mass |
| $m_b$ | Design blade mass |
| $f_{0,i}$ | Design blade natural frequency |
| $\Delta f_{span}$ | Expected blade mistuning |
| $f_{i,max}$ | Positive maximum of mistuning |
| $f_{i,min}$ | Negative minimum of mistuning |
| $k_{b,i}$ | Blade stiffness |

What is claimed is:

1. A method for determining blade mistuning on integrally manufactured rotor wheels for compressors/turbines, comprising:
    pulse-exciting individual blades one after another in a condition largely decoupled from other blades;
    measuring a vibratory response of the excited blade as an initial value for mistuning calculation;
    additionally mistuning blades not under investigation by temporarily applying an identical extra mass to each of the blades not under investigation, thereby shifting coupling effects originating from the blades not under investigation and disturbing measurement of the vibratory response of the blade under examination away from a natural frequency-near range of the blades and eliminating the coupling effects from measurement.

2. The method of claim 1, and further comprising determining an amount of the extra mass ($\Delta m$) depending on a design blade mass ($m_b$), a design blade natural frequency of the $i^{th}$ blade mode ($f_{o,i}$) and an expected magnitude of blade mistuning ($\Delta f_{span}$) as per:

$$\Delta m > m_b\left[\left[\frac{1}{1-\frac{|\Delta f|_{span} \div 100}{f_{0,i}}}\right]^2 - 1\right].$$

3. The method of claim 1, and further comprising establishing maximum frequencies ($f_i$) referred to respective amplitude maxima from transfer functions determined by measurement for each blade and family of modes, and using the maximum frequencies as input values for a relative blade frequency distribution ($f_i-f_{i,mean})/f_{i,mean}$) of the rotor wheel.

4. The method of claim 3, and further comprising correcting average values ($f_{i,mean}$) for the representation of the blade frequency distribution, which are calculated slightly too small, with a mass-spring-damper-model serving as an equivalent blisk model (EBM), with the frequency distribution determined by measurement being specified via an automated adaptation of the blade stiffnesses ($k_{b,i}$) to the equivalent blisk model thereby simulating pulse excitation from the measurement, and with the absolute blade natural frequency distribution for the determination of blade mistuning of the blisk in dependence of blade stiffnesses ($k_{b,i}$) and design mass ($m_b$) resulting from:

$$f_{b,i} = \frac{1}{2\pi}\sqrt{\frac{k_{b,i}}{m_b}}.$$

5. The method of claim 1, and further comprising providing the extra masses as small metallic cylinders and fixing them with a bonding agent to corresponding locations on the blades not under investigation.

6. The method of claim 5, and further comprising using beeswax as the bonding agent.

7. The method of claim 1, and further comprising producing an impact pulse for blade excitation using a miniature hammer and recording the vibratory response in a contactless manner with laser Doppler vibrometry.

8. The method of claim 7, and further comprising producing the impact pulse on the blades in each case at a same location and at a same angle.

9. The method of claim 1, and further comprising examining the rotor wheel borne in a removed state in a virtually free condition.

10. The method of claim 1, and further comprising examining the respective rotor wheel in an installed condition.

* * * * *